(12) United States Patent
Chen

(10) Patent No.: US 11,555,686 B2
(45) Date of Patent: Jan. 17, 2023

(54) NON-INTERDEPENDENT DISPLACEMENT MEASURING DEVICE FOR CONVERTING ROTARY MOTION TO LINEAR MOTION

(71) Applicant: BION INC., New Taipei (TW)

(72) Inventor: Yu-Yu Chen, Taipei (TW)

(73) Assignee: BION INC., New Taipei (TW)

( * ) Notice: Subject to any disclaimer, the term of this patent is extended or adjusted under 35 U.S.C. 154(b) by 456 days.

(21) Appl. No.: 16/745,573

(22) Filed: Jan. 17, 2020

(65) Prior Publication Data

US 2020/0249007 A1   Aug. 6, 2020

(30) Foreign Application Priority Data

Feb. 1, 2019   (TW) .................................. 108104027

(51) Int. Cl.
*A63B 24/00* (2006.01)
*G01B 7/14* (2006.01)
*A61B 5/00* (2006.01)
*G01D 5/12* (2006.01)

(52) U.S. Cl.
CPC ................ *G01B 7/14* (2013.01); *A61B 5/681* (2013.01); *A61B 5/6897* (2013.01); *A61B 5/6898* (2013.01); *A63B 24/0062* (2013.01); *G01D 5/12* (2013.01); *A61B 2562/0219* (2013.01); *A61B 2562/0223* (2013.01); *A63B 2220/40* (2013.01); *A63B 2220/836* (2013.01); *G01D 2205/22* (2021.05)

(58) Field of Classification Search
CPC ...... A63B 24/00; A63B 24/0087; G01D 5/12; G01D 2205/20; G01D 2205/22; G01D 2205/24; G01D 2205/26; G01D 2205/28; G01D 2205/70; G01D 2205/95
See application file for complete search history.

(56) References Cited

U.S. PATENT DOCUMENTS

2016/0054148 A1\*   2/2016   Misfatto ................. E05B 39/00
                                                                324/207.25

\* cited by examiner

*Primary Examiner* — Lawrence S Galka
(74) *Attorney, Agent, or Firm* — Chun-Ming Shih; HDLS IPR Services

(57) ABSTRACT

A non-interdependent displacement measuring device for converting a rotary motion to a linear motion is disclosed, which includes a driving unit, a detection unit, and a resistance device. The driving unit includes an adjustment section and a driving section. The detection unit is arranged in the adjustment section. The driving section is connected to the resistance device. The detection unit includes a sensing module and a transmission module, and the detection unit is arranged in the adjustment section, so that when the adjustment section rotates, the detection unit detects turns and an angle of rotation of the adjustment section to generate a detection signal, which, after being subjected to calculation, is transmitted through the transmission module to the electronic device to display the level of an resistance, so as to overcome the drawbacks of the prior art that accuracy is poor, calibration is difficult, and fabrication is difficult due to a magnet and a sensor being arranged as two separate parts.

12 Claims, 15 Drawing Sheets

Single Byte Write:

| Start Condition | Slave Address+RW | Ack | Register Address | Ack | Data | Ack | Stop Condition |

☐ : Master to Slave   ▨ : Slave to Master   Ack : Acknowledge

FIG.10A

Multiple Byte Write:

| Start Condition | Slave Address+RW | Ack | Register Address | Ack | Data | Not Ack | Stop Condition |

☐ : Master to Slave   ▨ : Slave to Master   Ack : Acknowledge

FIG.10B

Single Byte Read:

| Start Condition | Slave Address+RW | Ack | Register Address | Ack | Slave Address+RW | Ack | Data | Not Ack | Stop Condition |

☐ : Master to Slave  ▨ : Slave to Master  Ack : Acknowledge

FIG.10C

Multiple Byte Read:

| Start Condition | Slave Address+RW | Ack | Register Address | Ack | Repeat start Condition | Slave Address+RW | Ack | Data | Ack | Data | Not Ack | Stop Condition |

☐ : Master to Slave  ▨ : Slave to Master  Ack : Acknowledge

FIG.10D

NON-INTERDEPENDENT DISPLACEMENT MEASURING DEVICE FOR CONVERTING ROTARY MOTION TO LINEAR MOTION

BACKGROUND OF THE INVENTION

1. Field of the Invention

The present invention relates to a non-interdependent displacement measuring device for converting a rotary motion to a linear motion, and in particular to a non-interdependent displacement measuring device for use with a resistance adjusting knob of fitness equipment to convert a rotary motion to a linear motion.

2. The Related Arts

Modern fitness equipment, such as an exercise bicycle, is often provided with a resistance adjusting knob that regulates a level of resistance induced during exercise in order to achieve adjustment of strength of exercise to suit the specific needs for individuals, such that when the resistance is high, the consumption of calories caused by exercise is great, and oppositely, when the resistance is low, the consumption of calories caused by exercise is small, and accordingly, a desired result of exercise can be achieved.

Further, the way that the resistance adjusting knob adopts to regulate the resistance level is often such that the resistance adjusting knob causes a screw to drive a magnet on a resistance device to determine an active area thereof relative to a flywheel in order to determine the level of resistance. When the active area of the magnet and the flywheel is large, an eddy current induced by a magnetic field is large, so that a large magnetic acting force is generated, and oppositely, reduced magnetism is generated by a small acting force.

Further, in order to accurately calculate the amount of calorie consumed through use of fitness equipment, it often needs to acquire the level of resistance of exercise and related data, such as body height, body weight, and speed, are then employed to do calculation of an amount of work that an exerciser makes and the consumed amount of calorie.

However, prior art documents concerning acquisition of a level of resistance, such as Taiwan Utility Model M552361, which discloses "fitness equipment and sensor for application of resistance thereof", use a Hall sensor module to detect a magnetic field generated by a magnetic member for output of a detection signal. The detection signal varies with a change of a relative displacement of the magnetic member. As such, a torque analyzer is supplied with such a detection signal to thus acquire the distance between the magnetic member and the Hall sensor module and carries out analysis to determine the level of resistance that a resistance member currently applies to a torque generation unit thereby determining a current operation torque of the torque generation unit.

Such a known technique is effective in determining the level of resistance of exercise. However, when positional deviation occurs between the Hall sensor module and the magnetic member, the Hall sensor module is no longer effective in making measurement. Further, if a distance between the Hall sensor module and the magnetic member is excessively extended, the Hall sensor module is incapable of detection, while if the distance is excessively short, a detection signal between the Hall sensor module and the magnetic member may get excessively strong, leading to poor accuracy.

A general way of acquiring resistance relies on an interdependent fashion of combination of devices in order to carry out measurement of resistance. Such devices cannot work alone and must rely on another structure to perform measurement accurately. Examples include a combination of a reed switch and a magnet, an optical coupler, an encoder, a laser beam in combination with a reflector board. Such prior art interdependent devices refer to a structure that includes two separate parts, including a detector A and a magnet B, see FIG. 1, for use in fitness equipment. In addition to the previously mentioned Taiwan Utility Model M552361, other prior art documents, such as Taiwan Patent No. 1534420 and U.S. Pat. No. 9,314,667, are generally related to use of a two-part structure to carry out an operation of measurement. Such structures often suffer difficulty of fabrication due to issues of precision variation and difficulty of calibration between the magnet B and the detector A resulting from constraints or differences of fitness equipment. Further, fitness equipment is generally made of ferrous materials and would easily interfere with a magnetic field, leading to undesired situation of inaccuracy of data measurement. Thus, it is a challenge that needs to be urgently resolved in respect of accurately measuring resistance and allowing easy calibration or correction of a displaced sensor.

SUMMARY OF THE INVENTION

An objective according to the present invention is to provide a non-interdependent displacement measuring device for converting rotary motion to linear motion. The non-interdependent displacement measuring device is provided with a driving unit, a detection unit and a resistance device. The driving unit includes an adjustment section and a driving section having an end connected to the adjustment section. The detection unit includes a circuit board mounted on the adjustment section, a transmission module arranged on the circuit board, and a sensing module arranged on the circuit board and is electrically connected to the transmission module. The sensing module is operable to detect a number of turns and an angle of rotation of the adjustment section to generate a detection signal, and then the detection signal is transmitted through the transmission module to an electronic device. An opposite end of the driving section being connected to the resistance device.

Preferably, the circuit board further comprises a vibration detection unit provided thereon, so that when the adjustment section rotates, the vibration detection unit activates the sensing module and the transmission module into operation, and when the adjustment section stop rotation and stays in idle for a predetermined period of time, the vibration detection unit deactivates the sensing module and the transmission module.

Preferably, the circuit board further comprises an indicator provided thereon, the indicator being operable to display use time and power capacity of a power supply module, so that when the use time exceeds a predetermined maintenance interval or the power capacity is in a low level, the indicator issues an alarm message.

Preferably, the circuit board further comprises a calibration unit provided thereon, the calibration unit being operable to adjust starting-point and ending-point positions of the driving unit according to the number of turns and the angle of rotation of the adjustment section detected by the sensing module.

Preferably, the sensing module comprises a magnetometer.

Preferably, the sensing module comprises a combination of a magnetometer and a three-axis accelerometer.

Preferably, the electronic device comprises one of an electronic watch provided on an exercise device, a personal smart mobile device, a computer workstation, a gateway, and cloud.

Preferably, the adjustment section is connected to a housing to receive the detection unit to be mounted between the adjustment section and the housing.

Preferably, the power supply module comprises one of a rechargeable battery, a primary battery, and a module that supplies electrical power.

Preferably, the detection unit further comprises a display device that displays the detection signal or use time and power level of a power supply module, the display device being one of a liquid crystal display, a light-emitting diode display, and a device operable to display or indicate.

Preferably, the detection unit is further provided with a display device to display the detection signal or personal exercise data and physiological signals.

BRIEF DESCRIPTION OF THE DRAWINGS

FIG. 10A is a diagram illustrating a writing operation of a single byte of the magnetometer according to the present invention;

FIG. 10B is a diagram illustrating a writing operation of multiple bytes of the magnetometer according to the present invention;

FIG. 10C is a diagram illustrating a reading operation of a single byte of the magnetometer according to the present invention;

FIG. 10D is a diagram illustrating a reading operation of multiple bytes of the magnetometer according to the present invention;

DETAILED DESCRIPTION OF THE PREFERRED EMBODIMENTS

Figure 1:
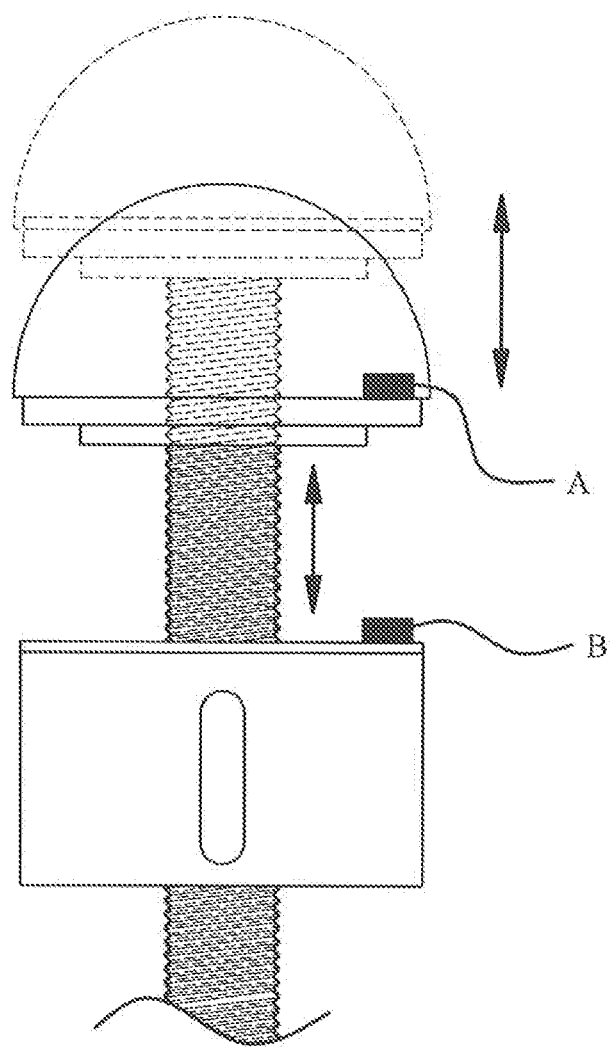
FIG. 1 is a schematic view showing a known structure.
Figure 2:
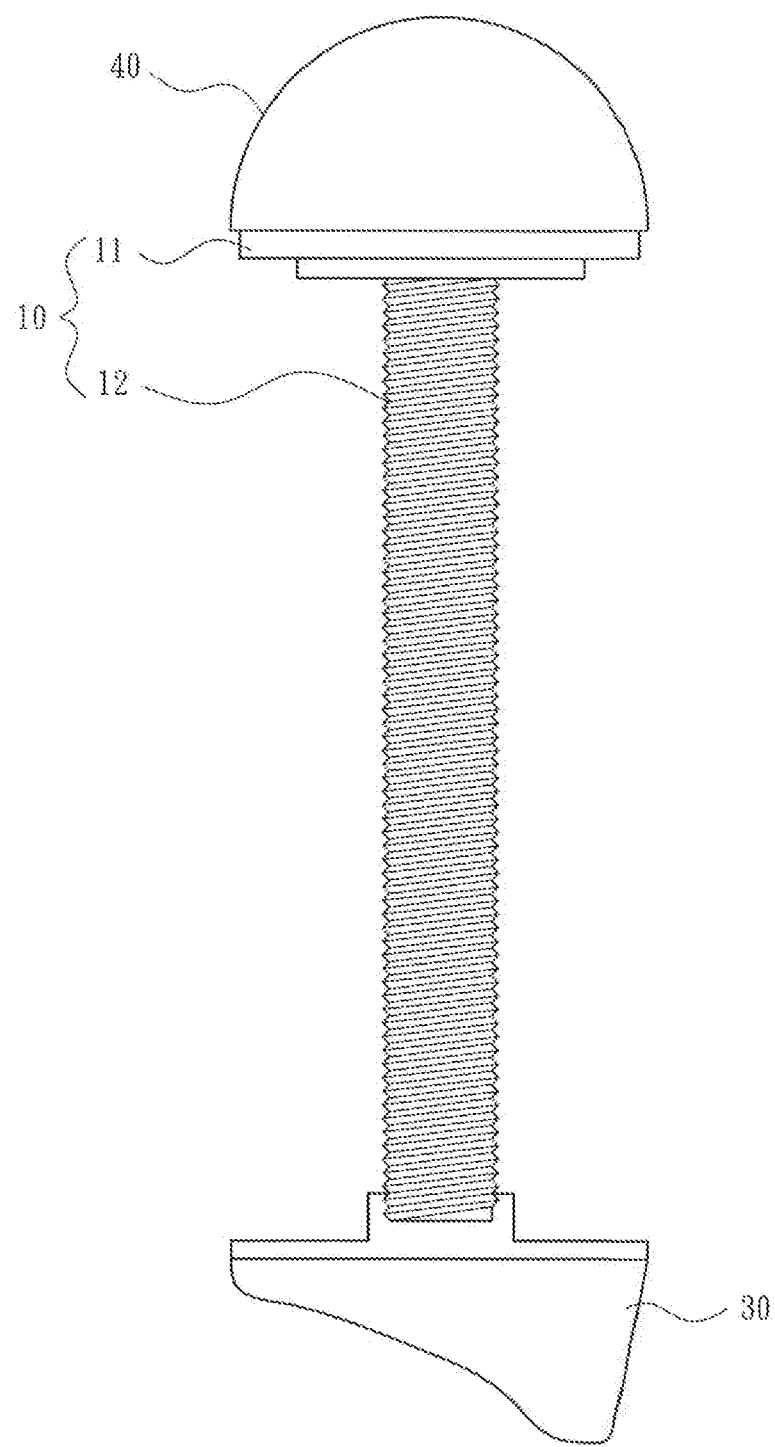
FIG. 2 is a schematic view showing a first embodiment of the present invention.
Figure 3:
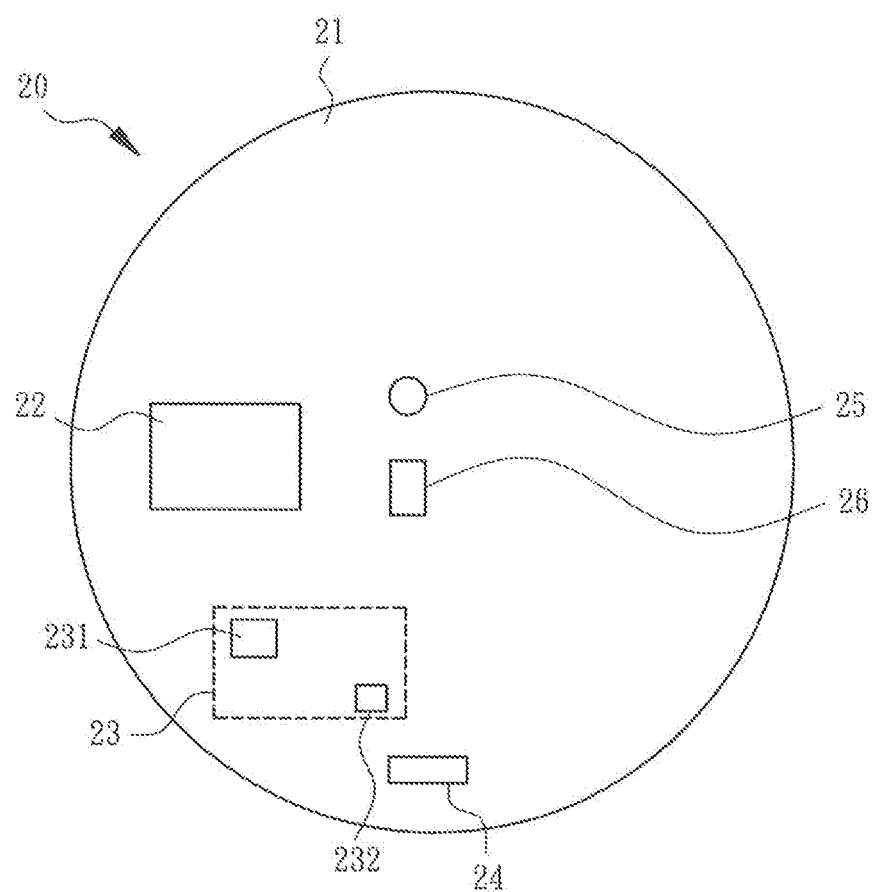
FIG. 3 is a schematic view showing a circuit board layout of the first embodiment of the present invention.
Figure 4:
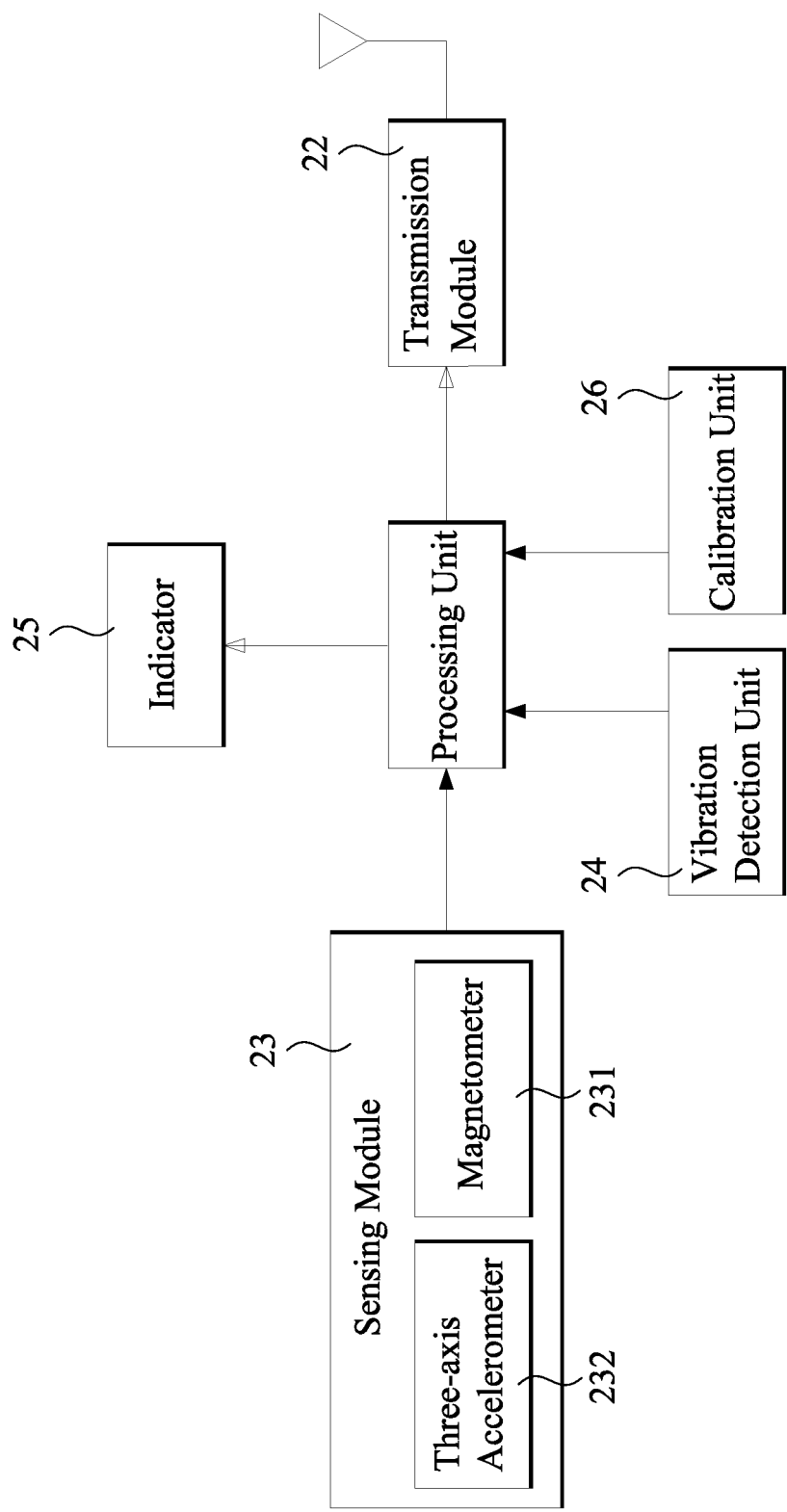
FIG. 4 is a block diagram of the first embodiment of the present invention.
Figure 5:
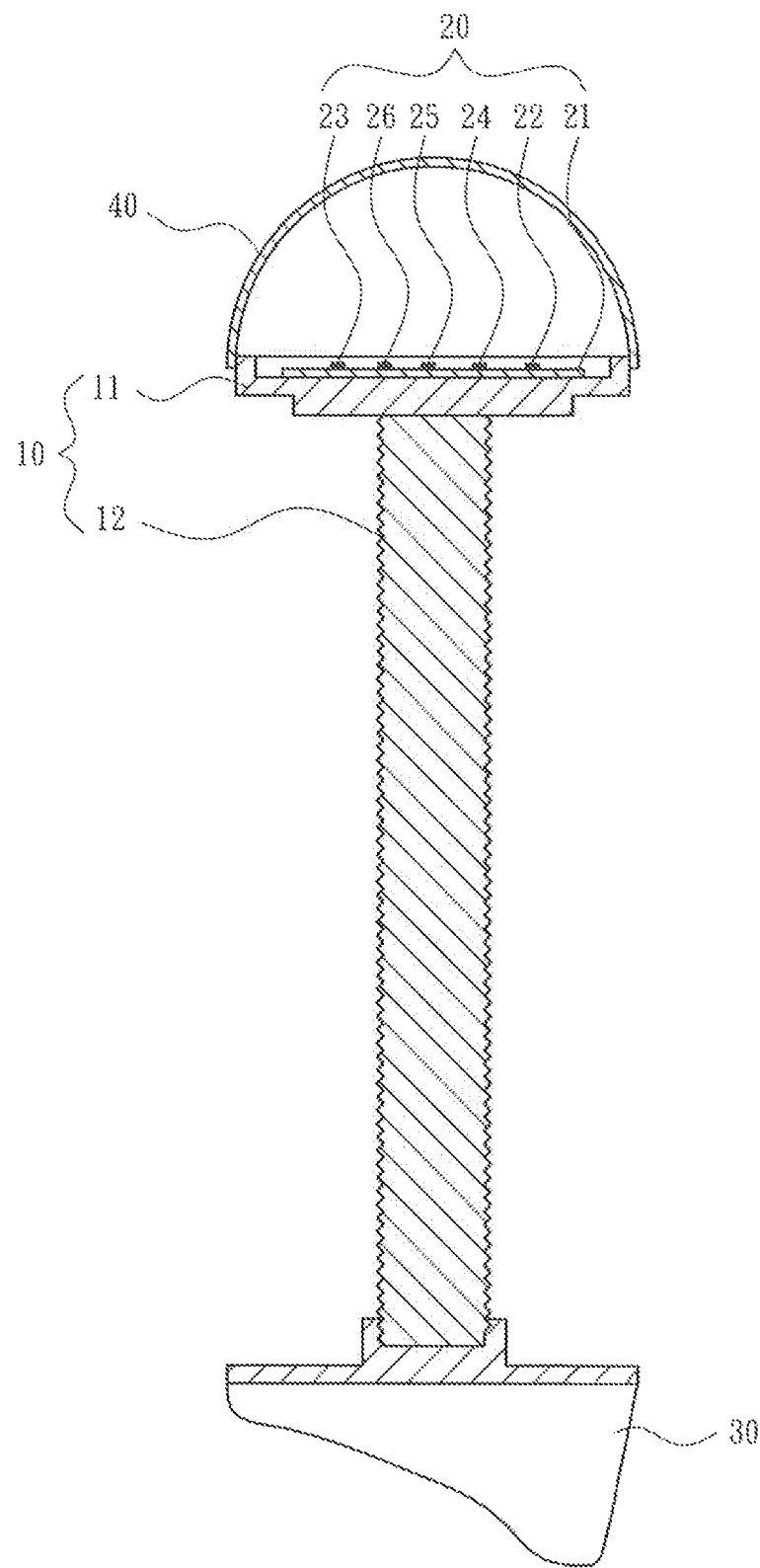
FIG. 5 is a cross-sectional view of the first embodiment of the present invention.
Figure 6:
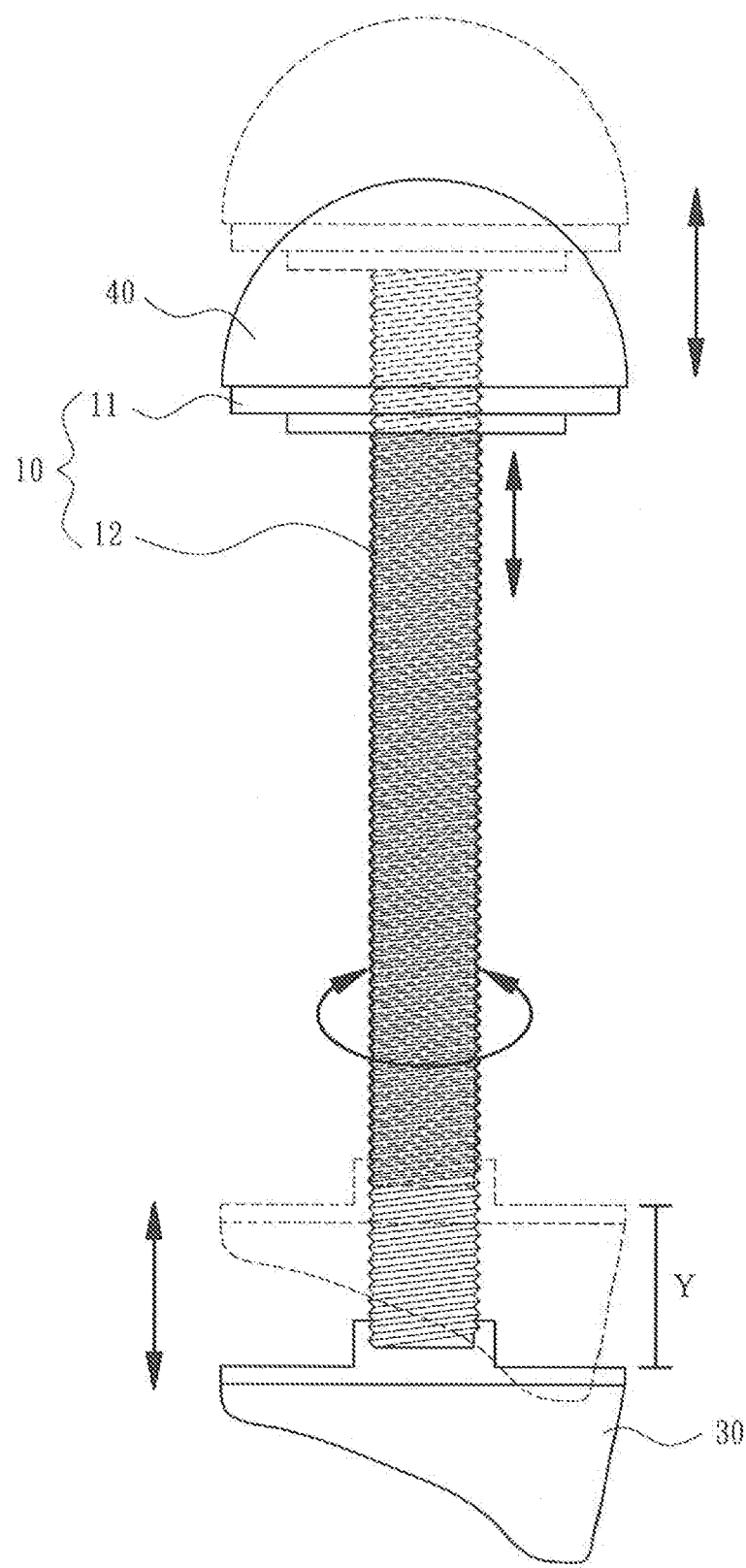
FIG. 6 is a schematic view showing a condition of operation of the first embodiment of the present invention.

A detailed description of the present invention will be provided below with reference to the attached drawings and embodiments of the present invention for better understanding of the purposes, technical solutions, and advantages of the present invention. It should be appreciated that the embodiments described herein are provided only for illustration and explanation of the present invention and are not intended to limit the present invention. Further illustration will be provided below with reference to the drawings:

Referring to FIGS. 2-5 and 9-12, the term "non-interdependency" as used in the present invention refers to a technology in which a detection unit is capable of working alone to complete a detection operation without being dependent on another structure/device. The present invention provides a first embodiment, which comprises a driving unit 10, a detection unit 20, and a resistance device 30. The driving unit 10 comprises an adjustment section 11 and a driving section 12. The driving section 12 has an end connected to the adjustment section 11 and an opposite end connected to the resistance device 30. As shown in FIGS. 3 and 5, the detection unit 20 is arranged in the adjustment section 11 and comprises a circuit board 21, a transmission module 22, a sensing module 23, a vibration detection unit 24, an indicator 25, and a calibration unit 26. The circuit board 21 is arranged on the adjustment section 11, and the transmission module 22 and the sensing module 23 are both provided on the circuit board 21. The transmission module 22 and the sensing module 23 are connected to each other. The adjustment section 11 is combined with a housing 40, so that the detection unit 20 is mounted between the adjustment section 11 and the housing 40. The housing 40 may be provided with a thread and the adjustment section 11 is provided with a thread corresponding to and is screwed to said thread in order to allow the housing 40 to be fixed, through screwing, to the adjustment section 11 in a manner of being removable through rotation or unscrewing for replacement a power supply module provided on the circuit board or to carry out repairing operations.

The sensing module 23 detects turns and angle of rotation of the adjustment section 11 to generate a detection signal. The detection signal is transmitted through the transmission module 22 to an electronic device to display a resistance level (not shown). The vibration detection unit 24 is provided such that when a user start rotating the adjustment section 11, the vibration detection unit 24 activates the detection unit 20 to start operating, and when the adjustment section 11 stays in idle, without being operated or activated, for a predetermined period of time, the vibration detection unit 24 shuts off or deactivates the detection unit 20 in order to reduce consumption of power. The indicator 25 functions to display use time and battery capacity of a power supply module (which can be a primary battery, a rechargeable battery, or other modules that provide electrical power). When the use time exceeds a predetermined maintenance time interval (indicating the use time is excessively long) or the battery is in a low level, the indicator gives off an alarm message in order to remind the user to shut down or deactivate the operation of the detection unit 20, or to remind the user of replacement of battery or supplementing electrical power. The calibration unit 26 can be specifically a correction switch that can be turned on or turned off selectively so that when the calibration unit 26, when turned on, is operable to adjust a starting-point and an ending-point positions of the driving unit 10 in accordance with the turns and angle of rotation of the adjustment section 11 detected by the sensing module 23.

Further, the sensing module 23 disclosed in the present invention include a magnetometer 231 and a three-axis accelerometer 232. The electronic device can be one of an electronic watch provided on an exercise device, a personal smart mobile device, a computer workstation, a gateway, or the cloud. The magnetometer 231 is operable to detect a direction by detecting geomagnetism.

Figure 9:
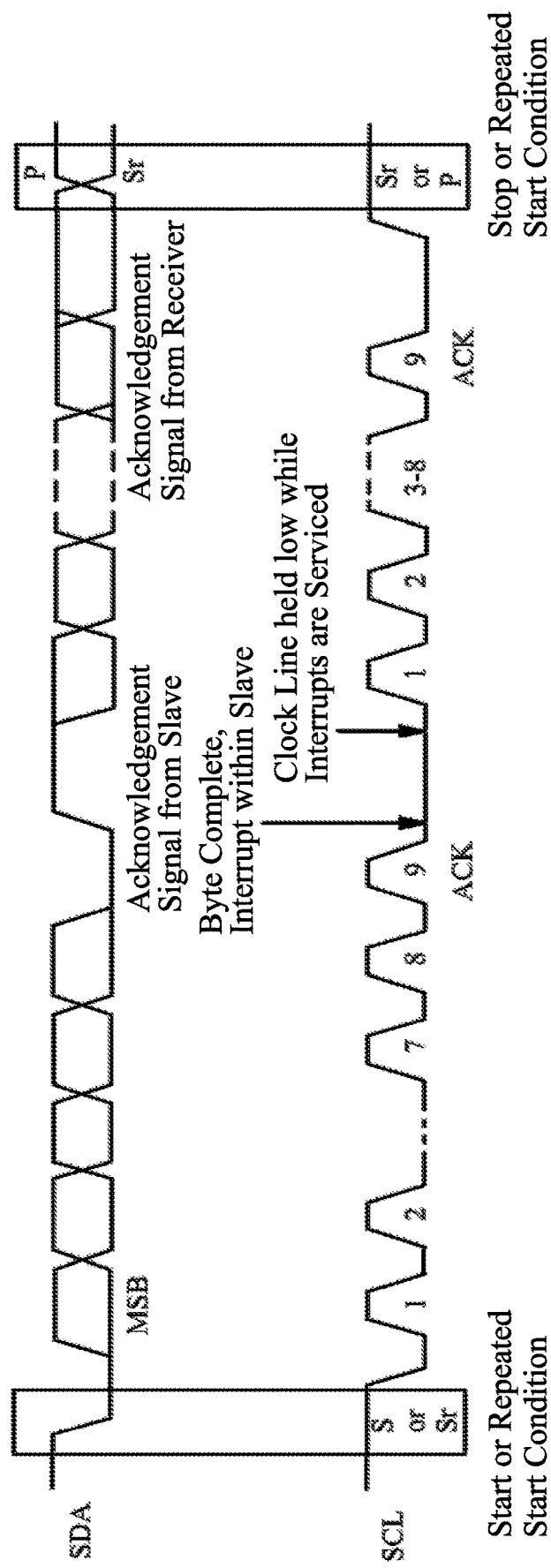
FIG. 9 is a diagram showing signal operation of a magnetometer of the present invention.
Figure 12:
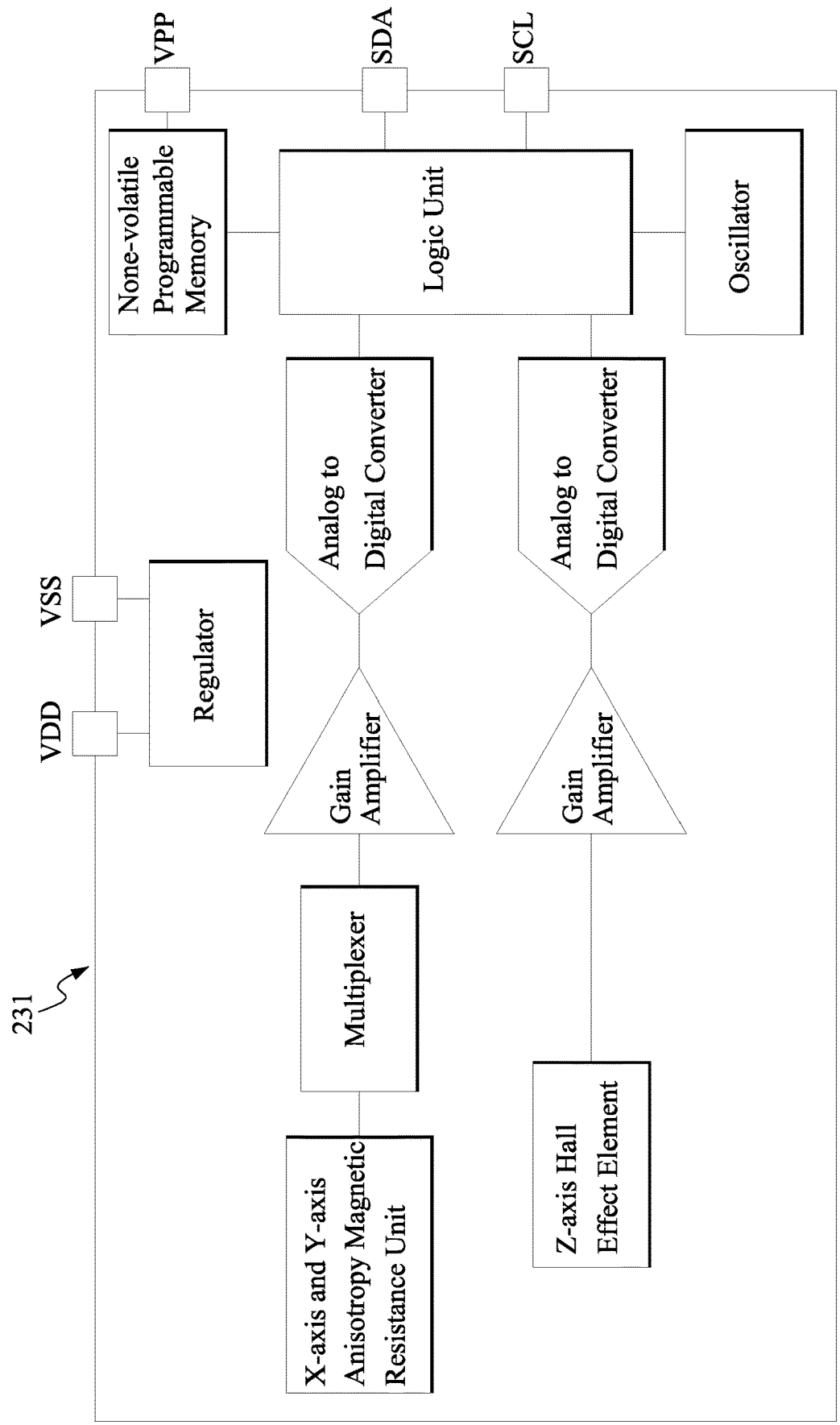
FIG. 12 is a block diagram of the magnetometer according to the present invention.

For example, a 3-axis digital magnetometer with commercial product number IST8312 can be used as the magnetometer 231. FIG. 12 is a block diagram of the magnetometer 231 according to the present invention. The magnetometer 231 provides a digital output with a regular mode (100 kHz) and fast mode (400 kHz). The magnetometer 231 is provided with a data line (SDA, Serial Data Line) and a clock line (SCL, Serial Clock Line). Pull-up resistors of 4.7 Kohm for both SDA and SCL lines should be used. FIG. 9 is a diagram showing signal operation of the magnetometer 231, starting with a start condition S, followed by data transmission, and finally ending with a stop condition P. The start condition is a specific combination of conditions of the data line and the clock line for the purposes of determination of start of the data transmission condition.

According to the above diagram of signal operations, address of a slave device is represented as follows:

| MSB bit 7 | bit 6 | bit 5 | bit 4 | bit 3 | bit 2 | bit 1 | LSB bit 0 |
|---|---|---|---|---|---|---|---|
| 0 | 0 | 0 | 1 | 1 | 0 | 0 | R/W | where MSB indicates the most significant bit and LSB indicates the least significant bit. The magnetometer 231 uses 7-bit slave address as OCH. If the magnetometer 231 uses 8-bit address, the slave address is 18H.

A writing operation of the magnetometer 231 can be classified as single byte writing and multiple byte writing (as shown in FIGS. 10A and 10B); and a reading operation is also classified as single byte reading and multiple byte reading (as shown in FIGS. 10C and 10D).

Figure 11:
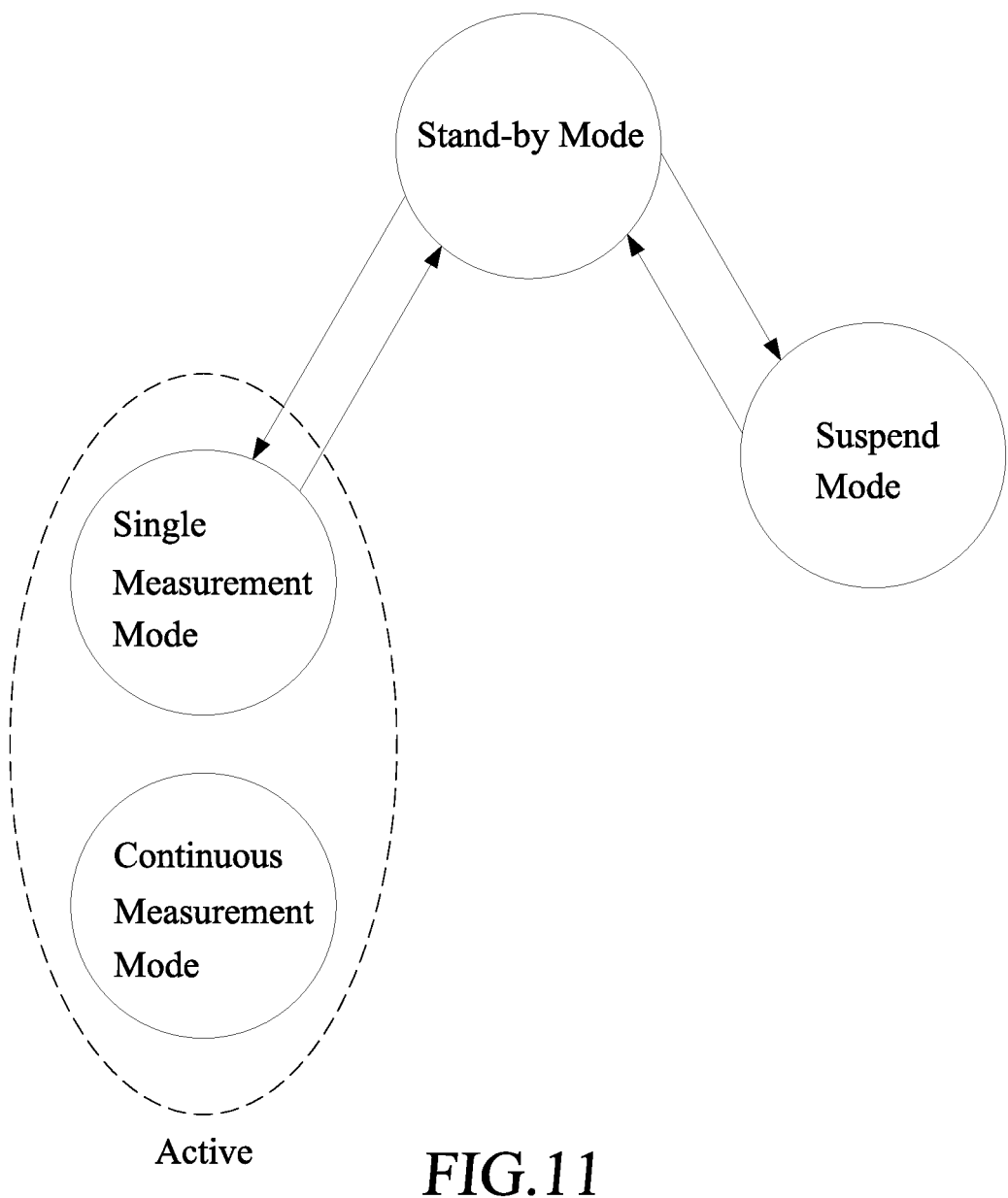
FIG. 11 is a diagram illustrating mode switching of the magnetometer according to the present invention.

The magnetometer 231 is operable in various operation modes including a single measurement mode, a continuous measurement mode, a suspend mode, and a stand-by mode (as shown in FIG. 11). The single measurement mode refers to the magnetometer 231 directly storing data detected thereby to a data storage and then switching to the stand-by mode. The continuous measurement mode refers to the magnetometer 231 performing measurements at a predetermined frequency within a given period of time, with detected data stored to the data storage, and when a next time period of detection arrives, the magnetometer 231 automatically re-starts measurement and data stored in the data storage is updated. The suspend mode refers to elements/devices other than those associated with a chip being shut down in order to allow the magnetometer 231 to maintain an operating condition at an extremely low level of power consumption. The stand-by mode refers to all elements/devices, except an oscillator (OSC) and a regulator, being shut down (as shown in FIG. 12).

Further, a component layout of the magnetometer 231 is such that components for detection in directions of three axes of X, Y, and Z are provided to detect a magnetic value of each of the directions in order to generate the detection signal. An arrangement of the three-axis accelerometer 232 is made for compensation of data detected by the magnetometer 231. For example, when installation of the present invention is excessively inclining, the three-axis accelerometer 232 may be put into operation for calculation in order to compensate the data detected by the magnetometer 231.

Referring to FIGS. 3-6, when a user rotates the adjustment section 11, the driving section 12, which is often combined with a solid object, rotates and drives the detection unit 20 to make displacement in a vertical direction or a horizontal direction (moving in the vertical direction being taken as an example in the instant embodiment). When the adjustment section 11 is rotated, the vibration detection unit 24 detects variation caused by such a motion and activates the detection unit 20 into operation so that the sensing module 23 instantaneously detects axial variations of the three axes (X-axis, Y-axis, and Z-axis) of the adjustment section 11 and thus detects the turns and angle of rotation of the adjustment section 11 to generate a detection signal. The detection signal is subjected to computation carried out by the sensing module 23 or a central processing unit and then transmission made through the transmission module 22, in a wired manner or a wireless manner, to transfer the detection signal to the electronic device, to allow the electronic device to subsequently use related data (such as body height, body weight, speed, and the likes) to calculate the amount of work made by an exerciser, a resistance level, and an amount of consumption of calorie.

In the rotation of the driving unit 10, since the sensing module 23 carry out detection using the axial variations of the X-axis, the Y-axis, and the Z-axis, a rotation direction of the driving unit 10 may also be detected at the same time when the turns and the angle of rotation are detected so as to determine whether the driving unit 10 rotates downward or upward. If the driving unit 10 rotates downward, since the opposite end of the driving section 12 is connected to the resistance device 30 (where the connection can be made through pivotal coupling), the resistance device 30 may be driven downward by the driving section 12 to increase the magnitude of resistance.

Oppositely, when a user uses the adjustment section 11 to cause the driving unit 10 to rotate upward, the sensing module 23 may use the detected values of turns and angle of rotation of the adjustment section 11 to calculate an amount of displacement (for calculating the resistance level), so as to generate the detection signal to be transmitted to the electronic device for calculating the amount of work and the amount of consumed calorie made by the exerciser. The resistance device 30 is correspondingly driven upward by the driving section 12 to thereby reduce the magnitude of resistance.

As such, by using the detection unit 20 to detect the detection signal generated by the adjustment section 11, the transmission module 22 may transmit the detection signal to the electronic device to carry out related operations of calculation and the detection signal can be supplied to a display device for displaying the detection signal or personal exercise data and physiological signal, and, by doing so, issues of the prior art, such as accuracy deviation, difficulty of calibration or correction, difficulty of measurement or fabrication resulting from the fact that a magnet and a sensor being arranged as two separate parts, can be overcome.

Further, the indicator 25 provided in the present invention may alternatively be arranged on the circuit board 21 in order to indicate use time of the present invention. When the use time exceeds a predetermined maintenance time interval, the indicator 25 indicates an alarm message to notify the user when the present invention needs to carry out a maintenance operation. Further, the indicator 25 may indicate a residual capacity of a battery, so that when the capacity of the battery is in a low level, the indicator 25 also gives off an alarm message to notify the user. Such an alarm message can any way including the indicator or a loud speaker.

Further, the calibration unit 26 provided in the present invention can be arranged on the circuit board 21. The calibration unit 26 is operable to adjust a starting position and an end position of the driving unit 10 according to the turns and angle of rotation of the adjustment section 11 detected by the sensing module 23. Specifically, when the sensing module 23 makes use of the adjustment section 11 rotating downward or upward, the calibration unit 26 starts a calibration or correction procedure to make adjustment of the starting-point position of the driving unit 10 for the adjustment section 11 rotating downward or upward and also to make adjustment of the ending-point position of the driving unit 10 for the adjustment section 11 rotating downward or upward to thereby complete the correction procedure, for automatically calculating the position in each section of stroke (from the starting point to the ending point).

With the fitness devices being of different structures, the number of resistance levels and lengths (moving strokes) for the driving section 12, total numbers of turns and angle of rotation of the adjustment section 11 may be different, among which the resistance level can be determined according to the equation: $Y=\theta/\Delta\theta+1$(level).

For example, when a total length of movement for the driving section 12 (the range of distance that the driving unit 10 is allowed to move in the vertical direction) is 25 mm, there are totally 30 levels of resistance (1st to 30th, with 29 intervals therebetween), a total number of turns of rotation is 10 turns (10×360 degrees=3600 degrees (total value of degrees)), wherein each interval is of a length or stroke=25 mm/29 intervals=0.862 mm/1 interval, and the total value of degrees 3600 degrees/29 intervals=124 degrees/1 interval (an increment of one level of each rotation range of 124 degrees). Assuming the user makes a rotation of two turns and 30 degrees to achieve a moving distance Y ("Y" being illustrated in FIG. 6), the angle of the turns of rotation is that the angle ($\theta$): $\theta=360\times2+30=750$ degrees, which is placed in the equation: $Y=\theta/\Delta\theta+1$ (level) to determine the resistance levels after the moving distance Y being made is: 750 degrees/124 degrees+1(level)=7(levels). It can thus be known that the user has set the resistance level to the seventh level and the displacement is: 0.862 mm×6(intervals)=5.172 mm.

During calibration, the starting point is reset at the first level and the adjustment section is rotated to the 29th level (which is the ending point), to effectively record the total number of turns and the total value of degrees.

Figure 7:
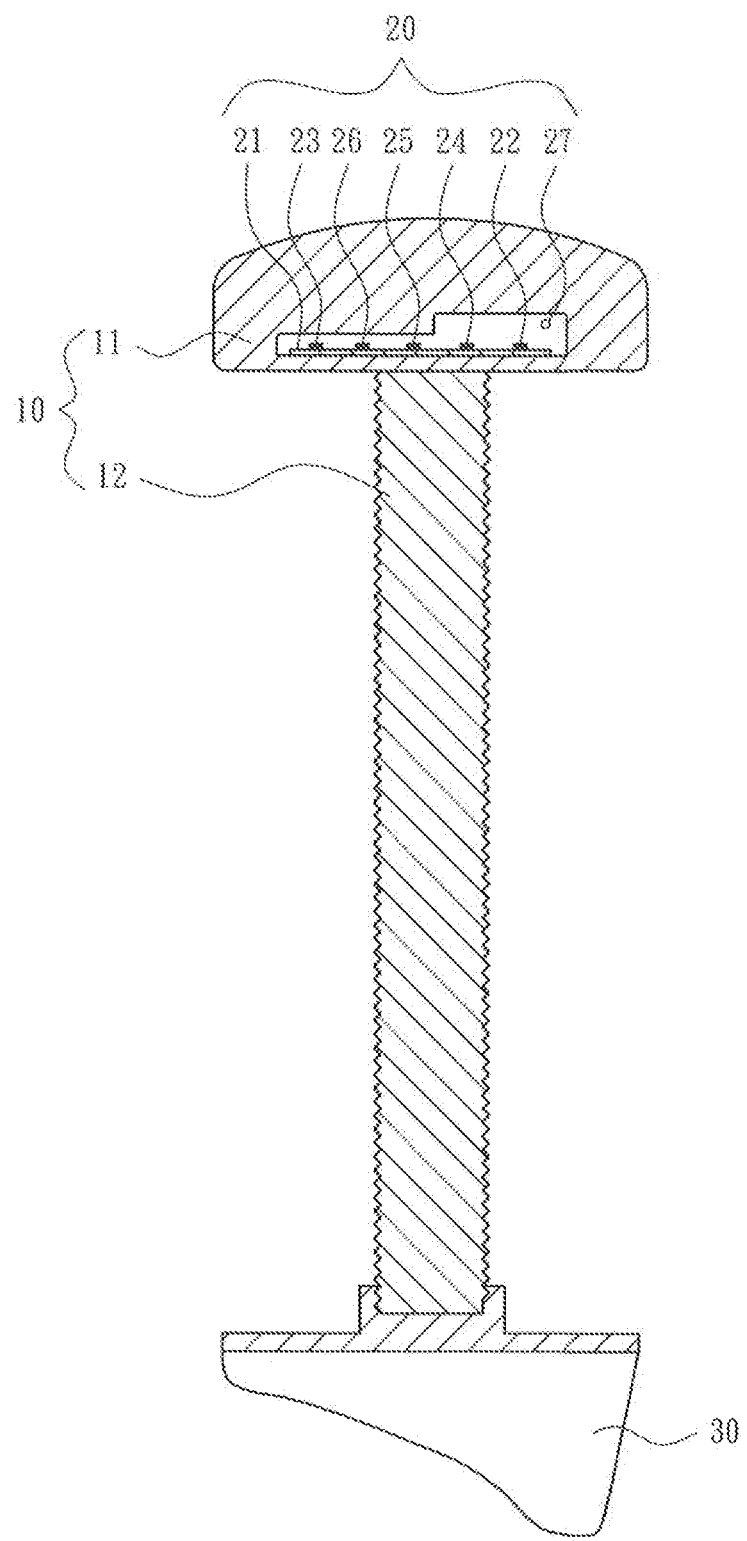
FIG. 7 is a cross-sectional view of a second embodiment of the present invention.
Figure 8:
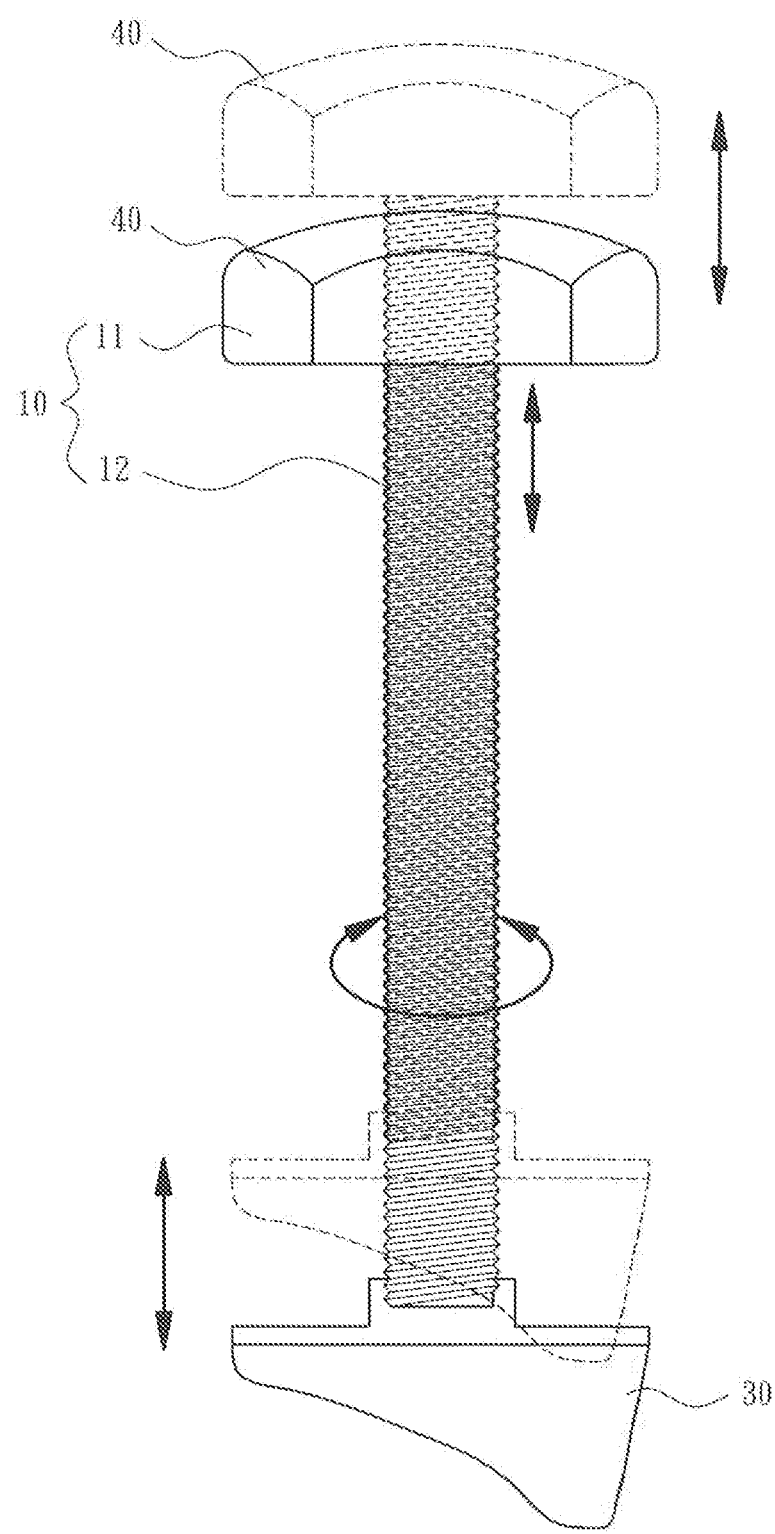
FIG. 8 is a schematic view showing a condition of operation of the second embodiment of the present invention.

Referring to FIGS. 7 and 8, which provide a cross-sectional view and a schematic view of a condition of operation of a second embodiment of the present invention, additional reference being had to FIG. 3, as shown in these drawings, in the second embodiment of the present invention, the housing 40 of the first embodiment may become unnecessary, and as such, in the instant embodiment, the adjustment section 11 can be made in other shapes and can also be formed in an integral form, and then, the circuit board 21, the transmission module 22, the sensing module 23, the vibration detection unit 24, the indicator 25, and the calibration unit 26 are arranged in an interior of the adjustment section 11. However, the circuit board 21, the transmission module 22, the sensing module 23 may be further arranged inside a detection shell 27 to effectively protect the circuit board 21, the transmission module 22, and the sensing module 23 from damage caused by an external force or other external environmental factor. As such, the present invention can be embodied in various combinations or structural arrangement to provide the same effectiveness.

Figure 13:
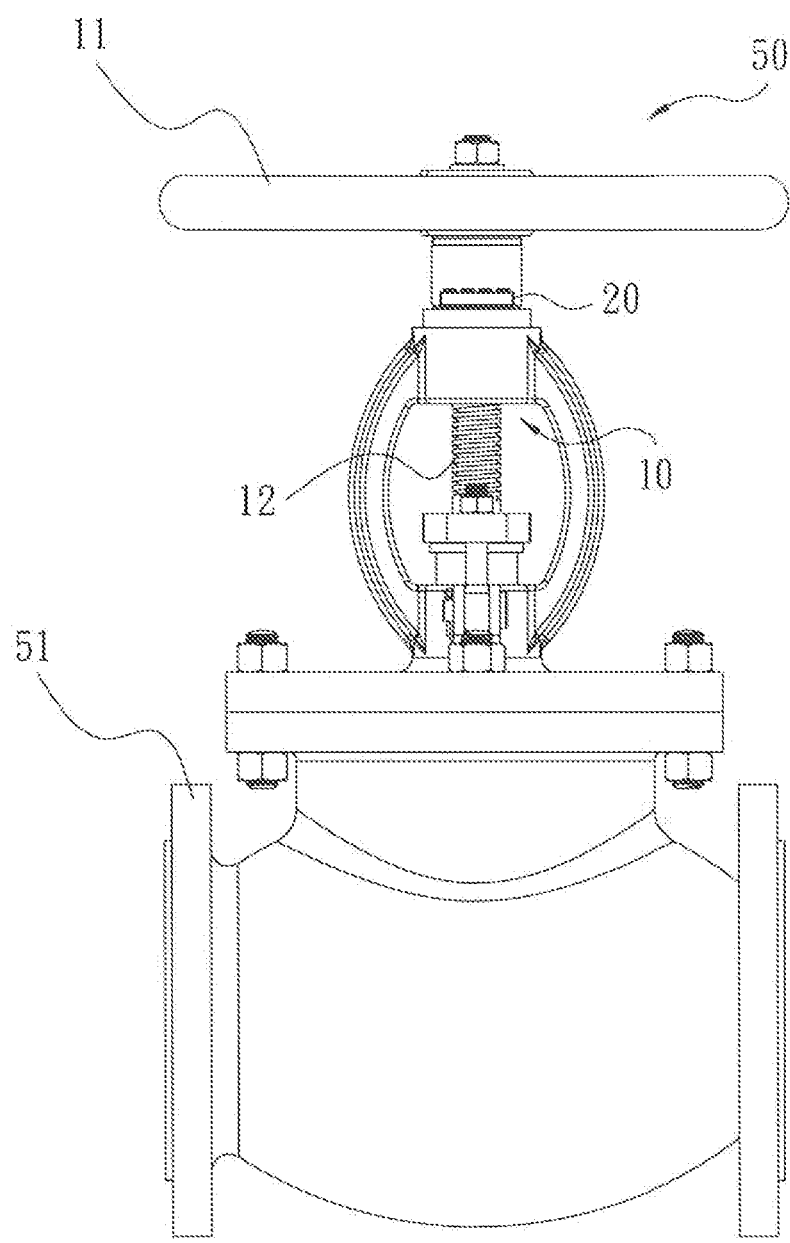
FIG. 13 is a schematic view illustrating application of the non-interdependent displacement measuring device for converting a rotary motion to a linear motion according to the present invention to a manual control valve.

The arrangement of the present invention can be used in a number of other devices for practical applications in order to better exploit the performance thereof. As shown in FIG. 13, which provides a schematic view illustrating the present invention being used with a manual control valve, the manual control valve 50 comprises an adjustment section (a hand wheel) 11 and a detection unit 20. The number of turns that the adjustment section 11 is rotated can be used to adjust a valve gate opening size of a valve body 51. Assuming an adjustment screw controlled by the valve body 51 is the driving section 12, the adjustment section 11 of the driving unit 10 may make direct control of the valve body 51 by means of the driving section 12. Similarly, the adjustment section 11 is provided with the detection unit 20, and the driving section 12 is connected to a valve gate in an interior of the valve body 51 so that through detection of the number of turns that the adjustment section 11 makes and an angular displacement thereof, accurate control of the valve gate opening size of the valve body 51 can be achieved.

Figure 14:
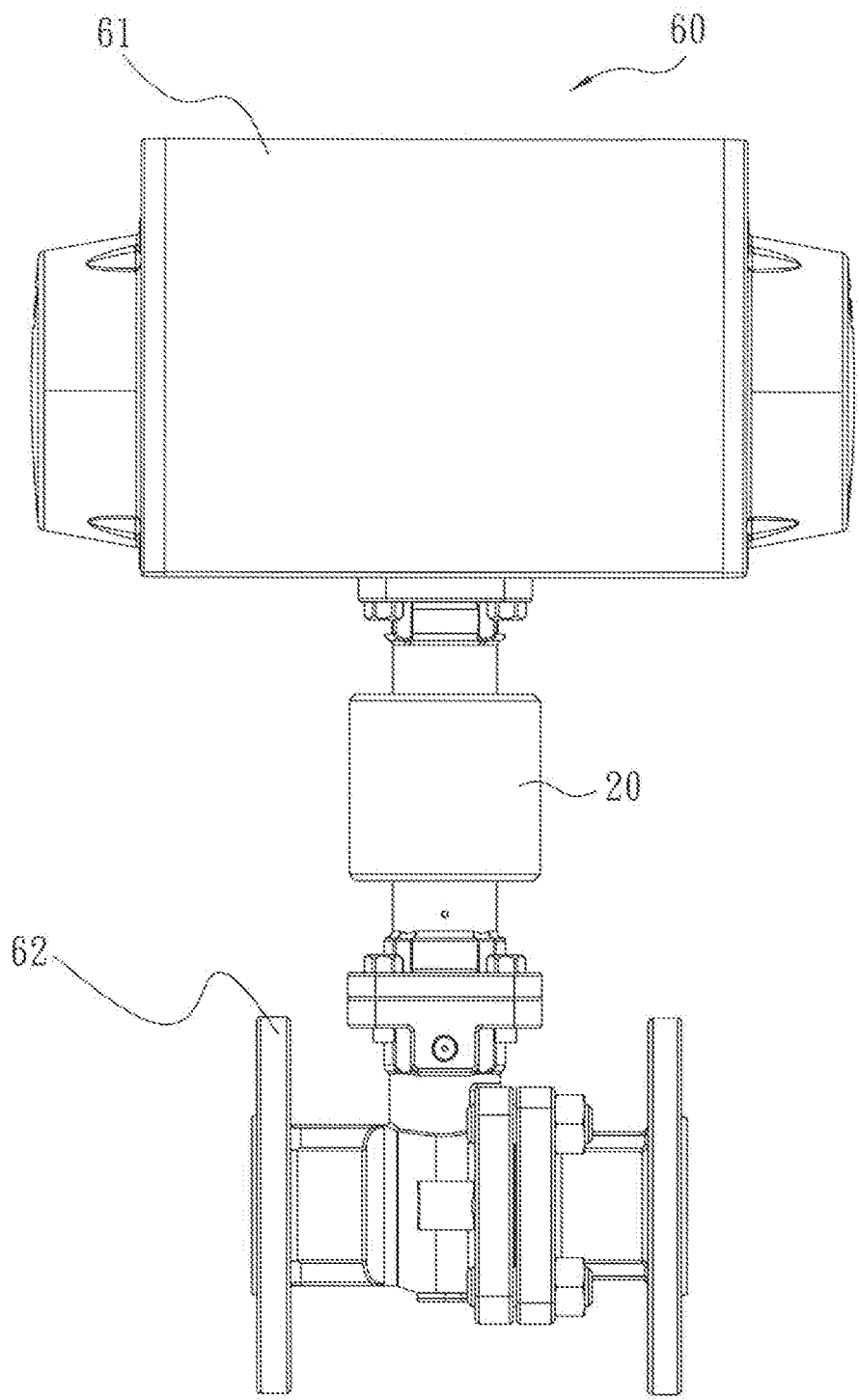
FIG. 14 is a schematic view illustrating application of the non-interdependent displacement measuring device for converting a rotary motion to a linear motion according to the present invention to an electric control valve.

Or, alternatively, as shown in FIG. 14, which provides a schematic view illustrating the present invention being used with an electric control valve, the electric control valve 60 comprises a driver unit 61 and a valve body 62, and for example, the driver unit 61 may be used to rotate and adjust the valve gate opening size of the valve body 62. Similarly, the adjustment section 11 of the driving unit 10 uses direct control of the driver unit 61 (wherein a site where the driver unit 61 drives the driving section 12 to rotate or a solid object to which to which the driving section 12 is fit to or fixed to so that the solid object and the driving section 12 are rotated in unison can be regarded as the adjustment section 11), and the adjustment screw controlled by the driver unit 61 serves as the driving section 12, and then, the detection unit 20 is provided on the adjustment section 11 and the driving section 12 is connected to the valve body 62, so that through detection of the number of turns that the driver unit 61 makes, accurate control of the valve gate opening size of the valve body 62 can be achieved.

Through the description of the structure and operation provided above, in addition to use with fitness equipment, such as a rowing machine, a weight training apparatus, a flywheel bike, and an exercise bicycle, the present invention can also be used in a steering wheel, an electric vehicle, a yacht, automatic navigation, or marine, on-land, or air-borne sports, so that a valve monitor system measures a rotation angle valve gate. The present invention provides the following advantages:

(1) Non-interdependent detection is provided to improve drawbacks resulting from structural constraint.

(2) Disassembling and assembling are easy.

(3) Precision is high and accurate detection signals are provided.

(4) Calibration is easy.

It should be noted that, in the description of the present invention, terms, such as "center", "lateral", "up", "down", "left", "right", "top", "bottom", "internal", and "external", which are used in indicating directions or positional relationships are defined on the basis of the directions and positional relationships observed on the drawing sheets and are provided for easy description of the present invention and for simplification of illustration, and are not intended to imply that any device or element as indicated thereby must be set in a specific direction or must be operated with a specific direction and a specific structure, and should not be construed as constraints to the present invention.

The above embodiments are provided to illustrate and explain the present invention, and they are not intended to limit the scope of the present invention. Equivalent modifications or substitutes that do not depart from the spirit of the present invention are considered falling in the scope of the appended claims.

What is claimed is:

1. A non-interdependent displacement measuring device for converting rotary motion to linear motion, comprising:
   a driving unit including:
      an adjustment section, and
      a driving section having a first end thereof connected to the adjustment section;
   a detection unit including:
      a circuit board mounted on the adjustment section, the circuit board including an indicator provided thereon, the indicator displaying a use time and a power capacity of a power supply module, wherein when the use time exceeds a predetermined maintenance interval or when the power capacity is at a low level, the indicator issues an alarm message,
      a transmission module arranged on the circuit board, and
      a sensing module arranged on the circuit board and electrically connected to the transmission module, the sensing module detecting a number of turns and an angle of rotation of the adjustment section and generating a detection signal responsive thereto, and the detection signal being subsequently transmitted through the transmission module to an electronic device; and
   a resistance device connected to an opposing end of the driving section.

2. The non-interdependent displacement measuring device according to claim 1, wherein the circuit board further includes a vibration detection unit provided thereon, wherein when the adjustment section rotates, the vibration detection unit activates the sensing module and the transmission module into operation, and when the adjustment section stops rotation and stays idle for a predetermined period of time, the vibration detection unit deactivates the sensing module and the transmission module.

3. The non-interdependent displacement measuring device according to claim 1, wherein the circuit board further includes a calibration unit provided thereon, the calibration unit being operable to adjust starting-point and ending-point positions of the driving unit according to the number of turns and the angle of rotation of the adjustment section detected by the sensing module.

4. The non-interdependent displacement measuring device according to claim 1, wherein the sensing module includes a magnetometer.

5. The non-interdependent displacement measuring device according to claim 1, wherein the sensing module includes a magnetometer and a three-axis accelerometer.

6. The non-interdependent displacement measuring device according to claim 1, wherein the electronic device includes one of an electronic watch provided on an exercise device, a personal smart mobile device, a computer workstation, a gateway, and cloud.

7. The non-interdependent displacement measuring device according to claim 1, wherein the adjustment section is connected to a housing to receive the detection unit to be mounted between the adjustment section and the housing.

8. The non-interdependent displacement measuring device according to claim 1, wherein the detection unit further includes a display device that displays the detection signal or the use time and a power level of the power supply module, the display device being one of a liquid crystal display, a light-emitting diode display, or a device operable to display or indicate.

9. The non-interdependent displacement measuring device according to claim 1, wherein the detection unit is further provided with a display device to display the detection signal or personal exercise data and physiological signals.

10. The non-interdependent displacement measuring device according to claim 1, wherein the resistance device includes a valve, the detection unit detecting the number of turns and the angle of rotation of the adjustment section to detect a valve gate opening size in an interior of the valve.

11. A non-interdependent displacement measuring device for converting rotary motion to linear motion, comprising:
    a driving unit including:
       an adjustment section, and
       a driving section having a first end connected to the adjustment section;
    a detection unit including:
       a circuit board mounted on the adjustment section,
       a transmission module arranged on the circuit board,
       a sensing module arranged on the circuit board and electrically connected to the transmission module, the sensing module detecting a number of turns and an angle of rotation of the adjustment section and generating a detection signal responsive thereto, and the detection signal being subsequently transmitted through the transmission module to an electronic device; and
       a display device displaying the detection signal or a use time and a power level of a power supply module, the display device being one of a liquid crystal display, a light-emitting diode display, or a device operable to display or indicate; and
    a resistance device connected to an opposing second end of the driving section.

12. A non-interdependent displacement measuring device for converting rotary motion to linear motion, comprising:
    a driving unit including:
       an adjustment section, and
       a driving section having a first end connected to the adjustment section;
    a detection unit including:
       a circuit board mounted on the adjustment section,
       a transmission module arranged on the circuit board,
       a sensing module arranged on the circuit board and electrically connected to the transmission module, the sensing module detecting a number of turns and an angle of rotation of the adjustment section and generating a detection signal responsive thereto, and the detection signal being subsequently transmitted through the transmission module to an electronic device; and
       a display device displaying the detection signal or personal exercise data and physiological signals; and
    a resistance device connected to an opposing second end of the driving section.

* * * * *